Figure 2:
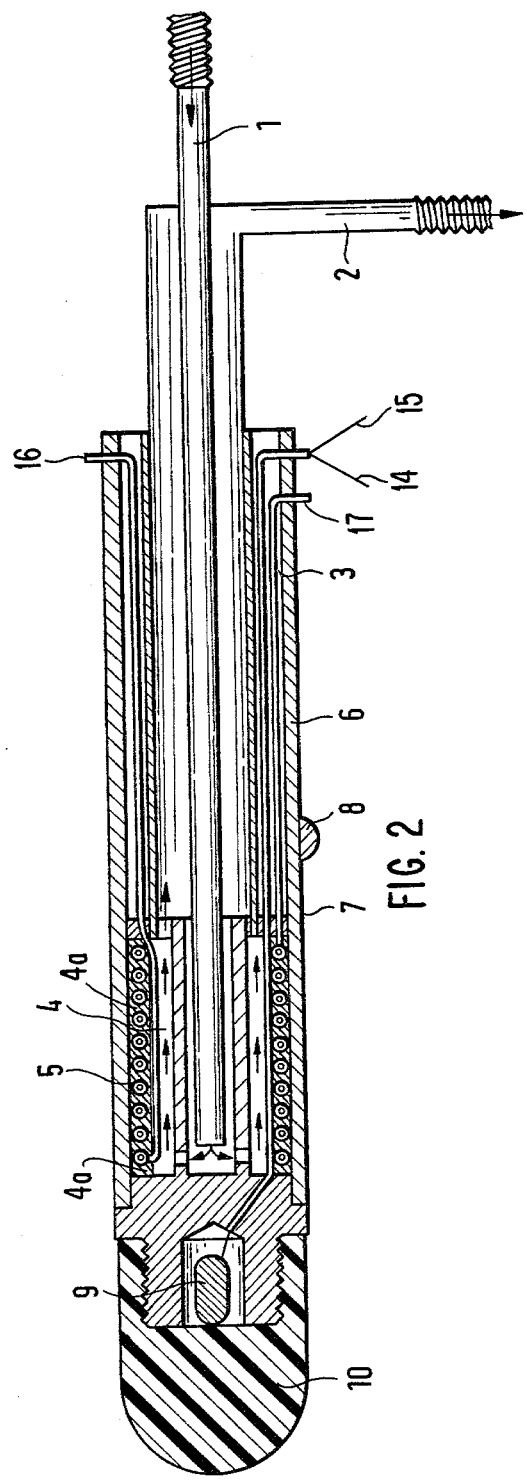

United States Patent [19]

van Gerven

[11] 4,202,336
[45] May 13, 1980

[54] CAUTERIZING PROBES FOR CRYOSURGERY

[75] Inventor: Hans van Gerven, Tübingen, Fed. Rep. of Germany

[73] Assignee: Erbe Elektromedizin KG, Tübingen, Fed. Rep. of Germany

[21] Appl. No.: 866,705

[22] Filed: Jan. 3, 1978

Related U.S. Application Data

[63] Continuation-in-part of Ser. No. 793,778, May 5, 1977, abandoned.

[30] Foreign Application Priority Data

May 14, 1976 [DE] Fed. Rep. of Germany ....... 2621553
Aug. 10, 1977 [DE] Fed. Rep. of Germany ....... 2736113

[51] Int. Cl.² .................................... A61B 17/36
[52] U.S. Cl. ................................... 128/303.1
[58] Field of Search ........... 128/303.1, 303.13, 303.14, 128/303.15, 303.17, 303.18, 399, 400, 401

[56] References Cited

U.S. PATENT DOCUMENTS

| 3,439,680 | 4/1969 | Thomas, Jr. | 128/303.1 |
| 3,507,283 | 4/1970 | Thomas, Jr. | 128/303.1 |
| 3,651,812 | 3/1972 | Samuels | 128/303.18 |
| 3,685,518 | 8/1972 | Beverle et al. | 128/303.17 |
| 3,736,937 | 6/1973 | Basiulis | 128/303.1 |
| 3,902,494 | 9/1975 | Haberlen | 128/303.17 X |
| 3,951,152 | 4/1976 | Crandell et al. | 128/303.1 |
| 3,971,383 | 7/1976 | Gerven | 128/303.1 |

FOREIGN PATENT DOCUMENTS

| 2258333 | 5/1974 | Fed. Rep. of Germany | 128/303.1 |
| 2315075 | 12/1974 | Fed. Rep. of Germany | 128/303.1 |
| 326952 | 3/1972 | U.S.S.R. | 128/303.1 |

Primary Examiner—Lee S. Cohen
Attorney, Agent, or Firm—Flynn & Frishauf

[57] ABSTRACT

A heating coil close to the freezing tip of a cryosurgical probe operates through a highly heat conductive portion of the probe wall so as to cauterize previously frozen tissues. The liquid nitrogen supply is continued long enough to cool the cauterizing surface to body temperature after the heating winding is switched off, after which the probe is withdrawn. An insulating spacer member on the end of the tip prevents unintended freezing of the bladder wall when the instrument is used for an operation on the prostate gland. The use of general anesthesia in such an operation is avoided by the use of the new probe. A probe for cauterizing only, for use after freezing by a conventional cryosurgical probe has the same kind of heater, temperature sensor and insulating tip but is equipped for circulating cooling water rather than cryogenic flow in the cooling space.

10 Claims, 3 Drawing Figures

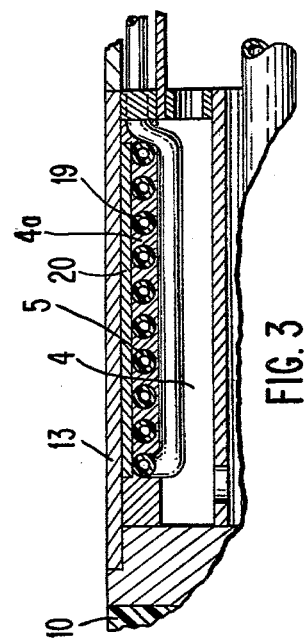
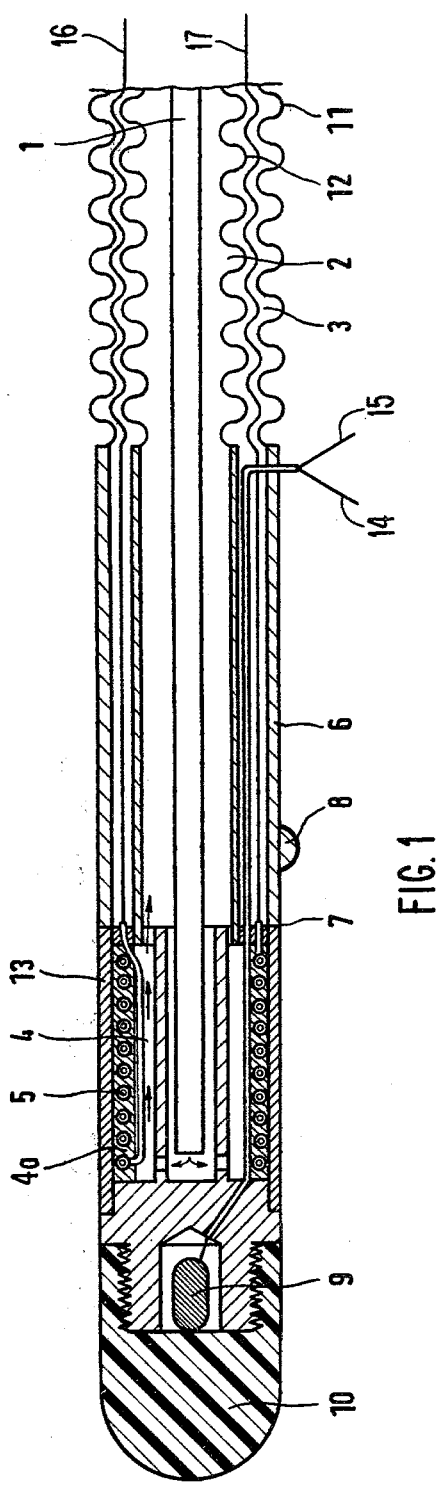
FIG. 3
FIG. 1

CAUTERIZING PROBES FOR CRYOSURGERY

This application is a continuation-in-part of my copending patent application, Ser. No. 793,778, filed May 5, 1977, now abandoned.

This invention relates to a cryosurgery using a probe of the kind having a tubular shaft with channels within the shaft for circulating a cryogenic medium to and from the tip of the shaft which is the refrigerating tip of the probe and has a thermometric sensor in the tip from which leads are brought out through the shaft for connection for appropriate instrumentation. Such probes are generally provided with a heating winding for thawing (defrosting) the probe at the end of a surgical freezing operation. The invention particularly concerns means for cauterizing tissues and includes both such means built into a cryosurgical probe and a special cauterizing probe for use after withdrawal, of a cryosurgical probe.

Known cryosurgical apparatus with probes of this type, as disclosed in published German application (OS) No. 24 22 103, are particularly used in surgical practice to freeze the prostate gland of a patient transurethrally for a maximum period of five minutes at −180° C. under local anesthesia. Thereafter, by use of general anesthesia, a transurethral resection can be performed. In contrast to this procedure, it is an object of the present invention to avoid, if possible, the use of any general anesthesia in such operations.

It is accordingly an object of the invention to improve cryosurgical probes of the kinds described above and to provide one of such characteristics that the tissue regions frozen by the probe can be cauterized by the probe itself. It is also an object of the invention to provide a cauterizing probe for obtaining the same effect following the use of a cryosurgical probe that is not equipped for cauterizing.

SUMMARY OF THE INVENTION

Briefly, the heating winding near the cold tip of a cryosurgical probe is so arranged and designed that instead of merely "defrosting" the probe, it is capable, immediately after a freezing operation, to produce a cauterization of flesh tissues in the region of the tissues frozen by the probe and, furthermore, the probe is provided with a coating, at least in its cauterizing portion, which is made of an elastomeric synthetic material that is stable at temperatures up to 200° C. and has the property of preventing the sticking of flesh to the probe during cauterization. This last named material is preferably a linear copolymer of vinylidene fluoride and hexafluoropropylene, a kind of material that is vulcanizable with polyamides, for example. Similarly, such a heater is provided in a probe of similar construction except for having means for circulating cooling water in the cooling space rather than a cryosurgical medium. Such a probe can be used for cauterization right after use of cryosurgical probe not equipped for cauterization.

The region of the probe shaft adjacent to the heating winding is preferably constituted of a sleeve of copper of low oxygen content having a nickel-plated outer surface. The heating winding preferably consists of a coiled conductor of nickel-chromium alloy wire, electrically insulated by magnesium oxide insulators and encircled by a protective shell of stainless steel, the outer surface of which is soldered or brazed to the inner surface of the copper sleeve. At the forward end of the cold tip a heating insulating spacing member is preferably provided that is made of a thermally stable synthetic resin material, which may be either the same material used for the elastomeric coating or polytetrafluoroethylene (PTFE), for example. Practical experiments have shown that after a freezing operation, the freezing end of the probe can very quickly be brought up to a temperature sufficiently high for cauterization in order to cauterize the region of frozen body tissues. Since the frozen tissues, as the result of anesthesia by cold, give no indication of pain when heated to about 200° C. when a cryothermic probe of the present invention is used, no supplemental general anesthesia is necessary, as for example in the case of transurethral resection. A further significant advantage of the kind of cryothermic treatment made available by the invention is that the patient is in most cases free of catheters after about four to six days, whereas in the usual cryosurgical treatment, four to six weeks are often necessary to reach that stage. The advantage of the heat insulating spacing member at the front end of the cooling tip, made of a thermally stable synthetic material, is to avoid unintended freezing and cauterizing of the bladder wall in the case of transurethral resections.

The invention is further described by way of illustrative example with reference to the annexed drawings, in which:

FIG. 1 is a diagrammatic longitudinal cross-section through a cryosurgical probe with built-in cauterizing equipment in accordance with the invention; and FIG. 2 is a longitudinal section through a cauterizing probe according to the invention for use after the withdrawal of a cryosurgical probe that is not equipped for cauterizing; and FIG. 3 is a detail of a preferred form of heating winding mounting for a probe according to the invention.

In the probe shown in FIG. 1. The supply tube 1 is surrounded by two concentric polyamide tubes 11 and 12 that confine an insulating space 3 filled with normal butane. The inner polyamide tube 12 defines, together with the facing outer wall of the supply tube 1, an intermediate space 2 that serves as the removal path for the gaseous nitrogen. In order to keep the polyamide tubes apart from one another, very thin stainless steel spacers, not shown in the drawing, are arranged in the intermediate space 2.

The probe itself, as distinguished from the tubular supply and removal ducts just mentioned, comprises a heat-insulating hollow cylindrical probe shaft 6 having an outer diameter of about 8 mm. A locating protrusion 8 is provided on the outside of the probe shaft 6 at an appropriate place in order that the correct position of the probe in the prostate gland can be determined. A hollow inner section 4 determines the region corresponding to the axial length of the probe over which the tissue surrounding the cooling tip can be frozen. In order that the liquid nitrogen can be vaporized as completely as possible in the probe, at the junction of the section 4 of the probe with the internal space providing the removal path of the gaseous nitrogen a liquid barrier is provided so that there is only a relatively small outlet slit for the passage of all of the nitrogen. In the hollow section 4, furthermore, a heating winding 5 is arranged. At the forward end of the cooling tip of the probe, there is arranged in the conventional way a temperature sensor 9 to the leads 14 and 15 of which there is connected, outside the probe, a resistance thermometer for control and monitoring, not shown in the drawing.

In accordance with the invention, the heating winding 5 is so designed and disposed in the section 4 that a temperature of about 200° C. can be obtained at the cooling tip with a heating power of about 120 watts. More generally, a temperature in the range between 170° C. and 205° C. should be reachable by a heating power between 100 and 150 watts. The heating winding 5 is energized through leads 16 and 17 and is in good heat conducting contact with the inner wall of the probe shaft 6. The hollow section 4 is filled with a porous material 4a with high heat conducting capability, preferably a sintered metal. The outer surface of the probe shaft 6 is encased in or coated with an elastomeric synthetic material that is thermally stable at about 200° C. (up to at least 205° C.) and that has the property of hindering the adhesion of tissues to the probe during cauterization. As this elastomeric synthetic there can be used a linear copolymer of vinylidene fluoride and hexafluoropropylene, a material that is for example vulcanizable with polyamides. Such synthetic materials, for example one commercially available under the name "Vinton" (trademark of the DuPont company) or PTFE, available under the name "Teflon" (trademark of the DuPont Company), are stable at temperatures up to 200° C. or even 205° C. and show no damaging chemical surface changes at the operating temperature used in probes according to the present invention. With such a coating, the adhesion of the cauterized tissues to the metal parts of the probe according to the invention can thus be avoided.

It is advantageous in practice to provide a heat-insulating spacer member 10 screwed onto the forward end of the cooling tip in order to prevent an unintended freezing or a cauterization of the bladder wall in a trans-urethral resection operation, for example. This spacer should be made of a temperature-stable synthetic material. This one-piece spacer 10 can be made of the same synthetic material as the coating 7 or it can conveniently be made out of polytetrafluoroethylene, a material commonly referred to as PTFE. In order to obtain a sufficiently good heat transfer, the forward end of the probe shaft 6, in the region of the heating winding 5, is preferably constituted by a sleeve 13 of copper having a low oxygen content, this lead having its outer surface nickel plated. Practical experiments have shown that low-oxygen copper is sufficiently resistant to corrosion on the inner side of the shell 13. A coiled heating conductor of chromium-nickel wire is particularly suitable for the heating winding 5. It is surrounded by magnesium oxide 19 for purposes of electrical insulation and further encircled in a protective shell of stainless steel 20 so that the outer wall of the heating element shell can be soldered or brazed to the inner wall of the sleeve 13. In this manner, a very good heat transfer during the freezing operation is obtained in the region of the shell 13, while on the other hand, the heat transfer capability is also provided that is necessary for the relatively high heating power in a small volume that is operative during activation of the heating winding 5. The end of the probe shaft 6 which is connected to the polyamide flexible tubes 11 and 12, on the other hand, consists of a material having good thermal insulating properties.

The mode of operation of the above-described probe will now be further explained. When a control valve provided for the nitrogen (not shown in the drawing) is opened, liquid nitrogen is supplied to the section 4 of the cooling tip, in order to vaporize there. The vaporized gaseous nitrogen then passes through the intermediate space 2 serving as its removal path and then through a discharge conduit not shown in the drawing to the atmosphere.

After the desired freezing temperature is reached, which is measured by means of the temperature sensor 9 of the resistance thermometer (the rest of which is not shown in the drawing), the switching over of the probe from freezing to cauterization is then performed, and the heating winding 5 is then heated at 120 watts power dissipation until the cauterization in the previously frozen tissue region is complete, when the heating winding is switched off. Shortly after the switching off of the heating winding, the probe can simply be withdrawn from the cauterized tissues if previous to the withdrawal nitrogen is still supplied through the supply conduit 1 long enough to cool down the probe tip to body temperature.

The performance of operations on many patients with a probe of the kind shown in FIG. 1 has also shown that no bleeding occurs in the removal of the dead tissue. This and the reduced pain and simplified after-treatment make it particularly desirable, in the interest of patients, for cryosurgical probes equipped with cauterizing means in accordance with the present invention to be introduced into medical practice as widely as possible and also, in the interest of economy, that the change in equipment should not necessarily require the replacement of existing cryosurgical equipment by probes with built-in cauterizing means. It is not readily possible, however, to build in a heating device suitable for cauterization within a previously known cryosurgical probe. Fortunately, by another aspect of the present invention, it is possible to use a probe of the kind illustrated in FIG. 2 to provide the benefits of the invention in the case of an operation performed with the use of a cryosurgical probe that does not have a built-in cauterizing heater. With the use of such a probe, the previously utilized cryosurgical probe is removed immediately after thawing and the cauterizing probe of FIG. 2 can then be inserted in its place. Since the cauterizing probe, after its insertion, can be then brought to the necessary temperature, with such cauterizing probes the essential advantages of the cryosurgical probe of FIG. 1 can be obtained with a probe according to FIG. 2 that is comparatively a simple and cheap supplementary device, provided that an existing cryosurgical probe is already available to perform the freezing step. The choice of material for the cauterizing probe of FIG. 2 can be made taking account only of the requirements that are of interest for cauterization, without regard to the requirements relating to cryosurgery that must be taken account of in the case of the probe of FIG. 1 and are described in detail above.

FIG. 2 shows conduits 1 and 2 respectively serving for supply and removal of cooling water to and from the probe. The probe is provided with a probe casing or shaft 6 in the shape of a metallic tube that at the cooling water inlet end surrounds an evacuated insulating space 3 and at the other end surrounds a cooling chamber 4 in which a heating winding 5 is provided. The length of the heating winding 5 and of the cooling chamber 4 corresponds to the region in which a patient's tissues can be frozen by means of a known cryosurgical probe. At the forward end of the probe shaft, a temperature sensor 9 is arranged in the same way as in the device of FIG. 1, likewise having a connection 11 for a resistance thermometer serving for control and monitoring or for some other temperature measuring system.

As in the case of FIG. 1, the heating winding 5 is so designed and is so located in the cooling space 4 that by a heating power of about 120 watts an external temperature of about 200° C. can be obtained in the tip portion of the probe. The heating winding 5 is set in good heat conducting contact with the inner wall of the probe shaft 6. The cooling space 4 is filled with a porous material of high heat conductivity, which material can for example be a sintered metal. The outside of the probe shaft 6 is encased in a coating of elastomeric synthetic material that is shrunk onto the shaft. The coating material must be thermally stable under heating to about 200° C. and its properties are selected so as to oppose or prevent the sticking of tissues to the probe during cauterization. At the forward end of the probe tip, a heat insulating spacing 10 is screwed on that can well consist of the same synthetic material used for the coating 7, for example polytetrafluoroethylene (PTFE). The spacer 10 serves to prevent an unintentional cauterization of the bladder wall.

The current supply for the heating winding 5 is provided through a connection lead 12. The heating winding 5 can consist of a heat element conductor made in the usual way from chromium-nickel wire that is surrounded by magnesium oxide for purposes of electrical insulation and is encased in a protective casing of stainless steel, so that the outer surface of the heating element can be soldered or brazed to the inner wall of the tubular probe shaft 10.

The manner of use of the cauterizing probe of FIG. 2 is as follows. For performing a prostate operation, first a cryosurgical probe not equipped with a built-in cauterizer is inserted and used and then removed after defrosting. The cauterizing probe is then introduced into the still frozen prostate and is positioned with assistance of the touching-up or dressing knob 8 correctly in the prostate. Then the heating winding 5 is heated up to about 200° C. and held at a constant temperature by means of a regulating system not shown in the drawing. After a heating-up time of about 1½ to 2 minutes, the heating winding can be turned off again. For cooling the cauterizing probe to body temperature, cooling water is circulated through the cooling space 4, being supplied and withdrawn respectively through the conduits 1 and 2. When the probe reaches body temperature as determined by the temperature sensor 9, it can be removed.

Although the invention has been described with reference to particular illustrative embodiments, it will be understood that variations and modifications may be made within the inventive concept.

I claim:

1. A surgical probe comprising a hollow tubular shaft having a metal tube portion forming an outer wall of the probe, said metal tube portion having an end region forming the end of said shaft and defining a cooling section of said probe, channels being provided within the shaft leading to and from said cooling section for circulation of a cooling medium, a tip connected to the extremity of said end region of said metal tube shaft portion and containing a thermal sensor and an electrical heating winding mounted in said cooling section of said shaft for thawing frozen tissues, and connecting means in said shaft associated with said heating winding for its energization by an external source of electricity, said probe having the improvement wherein:

the probe is provided with a coating (7) at least on the outer surface of said cooling section (4) thereof consisting of elastic synthetic material that is stable up to 200° C. and has the property of preventing the sticking of flesh to the probe even during cauterization;

material with good heat-conducting properties in contact with and close to the inner surface of said end region of said metal tube portion of said shaft which defines said cooling section (4);

the heating winding (5) is embedded in said heat-conducting material, makes firm contact with said metal tube portion therethrough and is of sufficient rating to be capable of raising said metal tube portion to a temperature of at least 190° C. at a power of at least 100 watts for not less than a few seconds, so that after a cryosurgical operation, a cauterization of flesh tissues in the region of tissues previously frozen can thereby be carried out, and;

said channels connect with a cooling cavity in said cooling section which is adjacent to said tip.

2. A surgical probe as defined in claim 1, in which said cooling section and said channels constitute means for the circulation of a cryogenic medium for causing said cooling section and said tip to freeze tissues for the purpose of a cryosurgical operation and said channels are provided, in the region of the end of said shaft remote from said tip, with inlets and outlets for a cryogenic medium, whereby with the very same probe at the very same place and immediately after a cryosurgical operation, a cauterization of flesh tissues in the region of tissues previously frozen can be carried out.

3. A surgical probe as defined in claim 2, in which the part of said metal tube portion of said shaft with which said heating winding is in contact is constituted by a sleeve (13) of copper of low oxygen content having a nickel-plated outer surface and located near said tip.

4. A surgical probe as defined in claim 3, in which said winding (5) consists of a coil conductor of nickel-chromium alloy wire, electrically insulated by magnesium oxide insulators and encircled by a protective shell of stainless steel, the outer surface of which is joined by a heat-integrated metal joint to the inner surface of said sleeve (13).

5. A surgical probe as defined in claim 2, in which at the end of said tip a heat-insulating spacing member (10) is provided that is made of thermally stable synthetic resin material.

6. A surgical probe as defined in claim 2, in which the heating winding (5) is so constituted that it can apply heat at a power of a minimum of 120 watts and thereby heat the probe surface to 200° C. in not more than 20 seconds.

7. A surgical probe as defined in claim 1, for service as a cauterizing probe for fitting into space vacated by a freezing probe in body tissue frozen thereby, in which:

said channels are provided, at the end of said shaft remote from said tip, with inlets and outlets for cooling water, and at least one electrical connection lead connected to said thermal sensor is brought out through said shaft.

8. A surgical probe as defined in claim 7, in which said electrical heating winding consists of a coiled conductor of nickel-chromium alloy wire, magnesium oxide insulation around said wire and a protective shell of stainless steel encircling said coiled wire conductor, the outer surface of which shell is joined by a heat-integrated metal joint to the inner surface of said metal tube portion of said tubular shaft.

9. A surgical probe as defined in claim 7, in which at the end of said tip a heat insulating spacing member (10) is provided that is made of thermally stable synthetic resin material.

10. A surgical probe as defined in claim 7, in which said heating winding is so constituted that it can apply heat at a power of a minimum of 120 watts and thereby heat the probe surface to 200° C. in not more than 20 seconds.